(12) United States Patent
Mantz

(10) Patent No.: US 6,527,011 B1
(45) Date of Patent: Mar. 4, 2003

(54) FLEXIBLE RETAINER RING FOR DUCK BILL VALVE

(76) Inventor: Robert F. Mantz, 2350 Woodlawn Cir. E., St. Petersburg, FL (US) 33704

( * ) Notice: Subject to any disclaimer, the term of this patent is extended or adjusted under 35 U.S.C. 154(b) by 0 days.

(21) Appl. No.: 09/573,801

(22) Filed: May 18, 2000

(51) Int. Cl.$^7$ .................... F16K 15/14; A62B 9/02; A61M 16/20
(52) U.S. Cl. ............... 137/848; 137/846; 137/908; 128/203.11; 128/205.24
(58) Field of Search ................ 137/102, 512.4, 137/846, 848, 856, 857, 908, 847; 128/203.11, 205.13, 205.24

(56) References Cited

U.S. PATENT DOCUMENTS

| | | | |
|---|---|---|---|
| 3,363,833 A | 1/1968 | Laerdal | 230/169 |
| 3,556,122 A | 1/1971 | Laerdal | 137/102 |
| 4,387,879 A | 6/1983 | Tauschinski | 251/149.1 |
| 4,622,964 A * | 11/1986 | Flynn | 137/102 |
| 4,774,941 A | 10/1988 | Cook | 128/205.13 |
| 4,942,873 A | 7/1990 | Irwin et al. | 128/203.11 |
| 4,974,586 A | 12/1990 | Wandel et al. | 128/206.28 |
| 4,993,452 A | 2/1991 | Hough | 137/515.7 |
| 5,103,854 A * | 4/1992 | Bailey et al. | 137/102 |
| 5,109,840 A | 5/1992 | Daleiden | 128/205.13 |
| 5,176,173 A | 1/1993 | McGarrah | 137/559 |
| 5,188,140 A | 2/1993 | Kosaka | 137/12 |
| 5,279,289 A | 1/1994 | Kirk | 128/205.23 |
| 5,343,858 A | 9/1994 | Winefordner et al. | 128/204.26 |
| 5,501,214 A | 3/1996 | Sabo | 128/205.24 |
| 5,655,520 A | 8/1997 | Howe et al. | 128/203.12 |

* cited by examiner

Primary Examiner—Michael Powell Buiz
Assistant Examiner—Ramesh Krishnamurthy
(74) Attorney, Agent, or Firm—Holland & Knight LLP

(57) ABSTRACT

An improved one-way valve for use in breathing apparatus comprising a valve housing, a one-way valve disposed in the valve housing that is in sealing contact to the valve housing, and a flexible retainer ring. The flexible retainer ring allows the one-way valve to unseat a greater distance within the valve housing thereby allowing an increase in the amount of expiratory gas through an exhaust port of the valve housing and the flexible retainer ring also prevents the deformation and inversion of the one-way valve thereby maintaining the proper flow of both respiratory and expiratory gases.

14 Claims, 6 Drawing Sheets

FLEXIBLE RETAINER RING FOR DUCK BILL VALVE

BACKGROUND OF THE INVENTION

The present invention relates in general to valve devices and, more particularly, to a valve adapted for use in breathing apparatus such as respiration assistance apparatus or anesthesia administration equipment.

FIELD OF THE INVENTION

Non-rebreathing valves, or NRVs, are commonly used in an assortment of anesthesia administration equipment and respiration assistance apparatus including, inter alia, ventilators, resuscitators and sleep apnea treatment devices. The NRV is typically situated in the breathing apparatus gas flow circuit between a source of respiratory gas (e.g., ambient or pressurized air, pressurized oxygen and/or anesthetic gas) and a patient interface means such as a nasal or oral/nasal mask, an endotracheal (intubation) tube or nasal prongs. The function of the NRV is to act essentially as a two-way check valve. More particularly, when it is desired to deliver respiratory gas to the patient, the NRV permits such flow. When the patient exhales, however, the NRV vents the patient's expiratory gases while temporarily stopping the flow of respiratory gas responsive to back pressure created by the patient's expiratory efforts. In this manner, the NRV effectively prevents mixing of the patient's expiratory gases with the delivered respiratory gas whereby the patient does not "rebreathe" his expiratory gases.

Although their functions are essentially the same, NRVs assume a broad variety of structural configurations and levels of functional sophistication. Because of its relative simplicity in construction and low resistance to administered respiratory gas flow, a commercially popular NRV is the type commonly known as a "duck-bill" valve. A duck-bill valve derives its name from the peculiar shape of its valve element. That is to say, a duck-bill valve element typically comprises a thin, resilient diaphragm that is secured at its periphery to a valve housing and from which projects, in the direction of administered respiratory gas flow, a hollow, wedge-like extension that terminates in a small slot and generally resembles the shape of a duck bill.

The duck-bill valve element is constructed such that its slot is normally closed. However, in response to a flow of respiratory gas, which may arise from negative pressure associated with a patient's inspiration and/or delivery of respiratory gas under positive pressure, the slot opens to permit the respiratory gas to flow to the patient's airway. When the patient thereafter exhales, the back pressure exerted by the patient's expiratory gases closes the slot and displaces the valve element from the valve housing seat whereupon the expiratory gases are diverted to and discharged from suitable exhaust port means provided in the valve housing.

Examples of presently known duck-bill valves are provided in U.S. Pat. Nos. 3,363,833, 3,556,122, 4,774,941, 5,109,840 and 5,279,289. Ironically, the primary feature which renders duck-bill valves particularly desirable for use in breathing apparatus, namely, a thin, flexible valve element that offers minimal resistance to respiratory gas flow, is a source of potentially serious malfunctions in such valves. Specifically, should the exhalation efforts of the patient be extremely forceful, such as, for example, when the patient coughs, the sudden imposition of high-level impulses of back pressure on the valve element may cause the duck-bill portion of the valve element diaphragm to invert. Under these circumstances, the duck-bill would point in the direction of the administered respiratory gas flow and the slot thereof would be caused to close under the influence of the applied respiratory gas. As a consequence, the supply of respiratory gas to the patient would become effectively occluded whereby the patient may experience harmful or even fatal respiratory distress, particularly if the patient is unconscious or is not being closely monitored by medical personnel.

Perhaps recognizing, although not specifically identifying, the need to prevent inversion of the duck-bill portions of their valve elements, the valves disclosed in U.S. Pat. Nos. 3,363,833, 3,556,122 and 5,109,840 disclose valve housings which incorporate various and sometimes elaborate structures upstream of the duck-bill which permit respiratory gas to flow through the duck-bill but, by virtue of their location, would appear to prevent the duck-bill from inverting. U.S. Pat. No. 5,279,289, on the other hand, expressly provides for a retainer ring upstream of the duck-bill valve element to "support" the valve element.

The retainer ring disclosed in U.S. Pat. No. 5,279,289 is designed to stay in a fixed position. Whereas, the present invention provides a flexible retainer ring having a center portion that can deflect in response to the duck-bill valve being moved by the flow of the expiratory gas. This movement of the flexible retainer ring of the present invention allows the duck-bill valve to unseat further from the valve housing seat thereby increasing the flow of the expiratory gas through the exhaust port of the valve housing. This increase in flow of expiratory gas to the exhaust port of the valve housing allows the valve housing to be made smaller than a conventional valve housing while maintaining the necessary flow rate for expiratory gas through the exhaust port of the valve housing. This smaller housing can be extremely useful in the care of infants and neonatal patients.

In addition, the flexible retainer ring of the present invention is able to provide better protection against inversion and distortion of the duck-bill valve. Since the flexible retainer ring is able to deflect in response to movement of the duck-bill valve, the flexible retainer ring is able to act as a shock absorber. This shock absorbing capability helps to prevent inversion and deformation of the duck-bill valve.

The flexible retainer ring of the present invention can also be employed in any industry needing to control the flow of two fluids in opposing directions.

An advantage exists, therefore, for a flexible retainer ring which is simple in design, economical to manufacture, and increases the flow of expiratory gas while preventing the inversion and distortion of the duck-bill valve element.

SUMMARY OF THE INVENTION

In accordance with the present invention, there is provided an improved duck-bill non-rebreathing valve (NRV) adapted for use in breathing apparatus such as anesthesia administration equipment and respiratory assistance apparatus. The duck-bill NRV may be situated in the breathing circuit between a source of respiratory gas (e.g., ambient or pressurized air, pressurized oxygen and/or anesthesia gas) and a patient interface means such as a nasal or oral/nasal mask, an endotracheal tube or nasal prongs.

The duck-bill NRV of the present invention comprises a thin, resilient valve element in the form of a diaphragm adapted to be secured at its periphery to a valve housing and from which projects, in the direction of administered respiratory gas flow, a hollow, wedge-shaped formation that terminates in a small slot and generally resembles the shape of a duck bill. The improvement in the NRV is the inclusion of a flexible retainer ring which has a center portion that that can deflect in response to the duck-bill valve being moved by the flow of the expiratory gas. This movement of the flexible retainer ring of the present invention allows the duck-bill valve to unseat further from the valve housing seat thereby increasing the flow of the expiratory gas through the exhaust port of the valve housing. This increase in flow of expiratory gas to the exhaust port of the valve housing allows the valve housing to be made smaller than a conventional valve housing while maintaining the necessary flow rate for expiratory gas through the exhaust port of the valve housing. This smaller housing can be extremely useful in the care of infants and neonatal patients.

In addition, the flexible retainer ring of the present invention is able to provide better protection against inversion and distortion of the duck-bill valve. Since the flexible retainer ring is able to deflect in response to movement of the duck-bill valve, the flexible retainer ring is able to act as a shock absorber. This shock absorbing capability helps to prevent inversion and deformation of the duck-bill valve.

According to a preferred embodiment, the improved non-rebreathing valve comprises a valve housing that has a first opening at one end, a second opening at an opposite end, an exhaust port in between the first opening and the second opening, and an internal valve housing seat. A one-way valve element is disposed in the valve housing between the first opening and the exhaust port. The one-way valve element is in sealing contact with the internal valve housing seat of the valve housing. A respiratory gas flows through the first opening, through the one-way valve element, continuing through the valve housing, and only out of the second opening and eventually reaching the patient. The patient expels an expiratory gas back through the second opening, into the valve housing to the one-way valve element. The one-way valve element blocks the flow of the expiratory gas and, as a result, is unseated from the internal valve housing seat. Once the one-way valve element is unseated, the expiratory gas can then flow to the exhaust port and out of the valve housing. The flexible retainer ring of the present invention allows the one-way valve element to unseat a greater distance from the internal valve housing seat thereby increasing the flow of the expiratory gas to the exhaust port of the valve housing.

In addition, the above preferred embodiment of the present invention provides for shock absorption through the flexible retainer ring in the event the patient expels with great force against the one-way valve element. The flexible retainer ring, constructed according to the present invention, prevents the deformation and inversion of the one-way valve element while allowing the continuous flow of the respiratory gas in an opposite direction.

According to an alternative embodiment, the improved one-way valve comprises a valve housing that has a first opening at one end, a second opening at an opposite end, an exhaust port in between the first opening and the second opening, and an internal valve housing seat. A one-way valve element is disposed in the valve housing between the first opening and the exhaust port. The one-way valve element is in sealing contact with the internal valve housing seat of the valve housing. A first fluid flows through the first opening, through the one-way valve element, continuing through the valve housing, and only out of the second opening. A second fluid or back flush of the first fluid returns back through the second opening into the valve housing to the one-way valve element. The one-way valve element blocks the flow of the second fluid or back flush of the first fluid and, as a result, is unseated from the internal valve housing seat. Once the one-way valve element is unseated, the second fluid or back flush of the first fluid can then flow to the exhaust port and out of the valve housing. The flexible retainer ring of the present invention allows the one-way valve element to unseat a greater distance from the internal valve housing seat thereby increasing the flow of the second fluid or back flush of the first fluid to the exhaust port of the valve housing.

With an NRV or one-way valve so constructed, the flexible retainer ring of the present invention allows the valve housing to be made smaller than a conventional valve housing while maintaining the necessary flow rate for the expiratory gas or second fluid through the exhaust port of the valve housing. This smaller housing can be extremely useful in the care of infants and neonatal patients or in industrial applications requiring smaller instruments. Further, the flexible retainer ring offers increased protection against inversion and effectively maintains the integrity of the one-way valve element while producing an assembly of uncomplicated yet rugged design, comparatively low cost to manufacture and reliable operation.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figures 1, 1A:
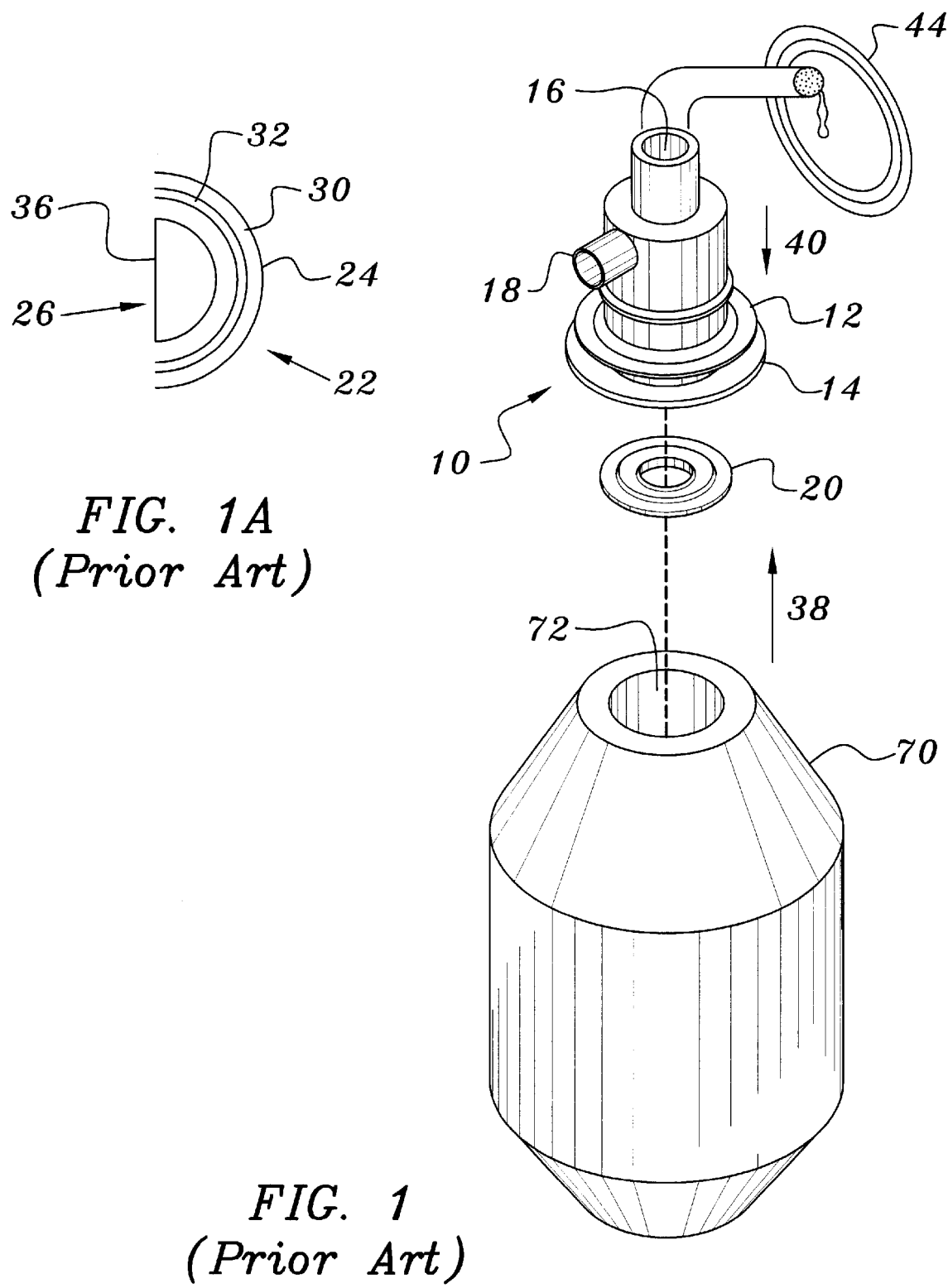
FIG. 1 is an exploded view of a conventional duck-bill NRV attached to a breathing assistance apparatus.
FIG. 1A is a blown up cross-sectional view of the duck-bill valve element within the valve housing of the NRV.

Referring to FIG. 1, there is depicted a conventional non-rebreathing valve (NRV) 10 attached to a breathing assistance apparatus. It is noted that for purpose of illustration, but not limitation, the breathing assistance apparatus is shown as a resuscitator apparatus commonly known as a "squeeze bag" or "bag-valve-mask" type resuscitator, the general operation of which is well known to those skilled in the subject art.

As best shown in FIG. 1, the NRV 10 includes a valve housing 12 having a first opening 14 at one end, a second opening 16 at an opposite end, and exhaust port 18 in between the first opening 14 and the second opening 16. The first opening 14 fits within the exit port 72 of the resuscitator bag 70.

A one-way valve element 20 is disposed within the valve housing 12 for directing the flow of a fluid. Resuscitator bag 70 delivers respiratory gas (e.g., ambient or pressurized air, pressurized oxygen or a combination of such gases) to a patient's airway through the one-way valve element 20 and a suitable patient interface means 44 such as a nasal or oral/nasal mask, intubation tube or nasal prongs. It will thus be appreciated that resuscitator bag 70 may also be, inter alia, a ventilator, a sleep apnea treatment apparatus or an anesthesia administration device.

Typically, the one-way valve element 20 is made in the shape of a duck's bill. As best shown in FIG. 1A, there is a blown up cross-sectional view of a duck-bill valve 22 within the valve housing 12. The duck-bill valve 22 shown comprises an outer peripheral portion 24 which is continuously and sealingly affixed to the valve housing 12 internally at a point between the first opening 14 and the exhaust port 18. In addition, the duck-bill valve 22 has an inner portion 26 that projects towards the second opening 16 of the valve housing 12. This inner portion 26 is hollow and wedge-shaped which generally resembles the shape of a duck's bill. At the distal end of the inner portion 26 is a small slot 36.

Typically, the duck-bill valve 22 is a unitary diaphragm member formed of thin, flexible, resilient material such as silicone rubber or the like. The outermost peripheral portion 24 of the duck-bill valve 22 is normally continuously and sealingly affixed by suitable adhesives and/or clamping means to the valve housing 12.

Extending radially inwardly of and contiguous with the outer peripheral portion 24 is a sealing portion 30 which may include a generally semi-toroidal region 32 for rendering the duck-bill valve 22 less resistant to the pressure generated by the patient's expiratory efforts. As is known, except when the patient is exhaling, the sealing portion 30 typically contacts an internal valve housing seat 34 and operates to effect a gas tight seal between the interior of the valve housing 12 and the exhaust port 18 provided in the valve housing 12 which communicates with the ambient atmosphere. This seal is further enhanced when the NRV 10 is delivering a respiratory gas 38 through the duck-bill valve 22 to the airway of the patient. Respiratory gas 38 is represented by arrow 38.

Regardless of the specific breathing apparatus within which it is deployed, the NRV 10, as is the NRV 10 of the present invention to be described hereinafter, is installed in the breathing circuit between a source of selected respiratory gas 38 and the patient interface means 44 such that the inner portion 26 of the duck-bill valve 22 points in the direction of the flow of the administered respiratory gas 38.

Whereas, should the patient exhale an expiratory gas 40, represented by arrow 40, or the respiratory gas 38 flow be stopped, the small slot 36 closes. Once the small slot 36 is closed, the patient's expiratory gases 40 flow in a direction opposite to the flow of the respiratory gas 38.

So long as the patient's respiration proceeds according to substantially uneventful phases of inspiration and expiration, the NRV 10 functions quite satisfactorily for its intended purposes. If, however, the patient's exhalation efforts become exceptionally forceful such as, for example, when the patient coughs, the sudden impingement of high-level impulses of back pressure on the inner portion 26 may cause the inner portion 26 to invert. Should this occur, the inner portion 26 would point in the direction of the administered respiratory gas 38 flow and the small slot 36 thereof would be urged to close under the influence of the applied respiratory gas 38. Such a scenario represents more than a simple inconvenience in that it temporarily disables the NRV 10. Indeed, under these conditions, the supply of respiratory gas 38 to the patient becomes effectively occluded, whereby the patient may experience harmful or possibly fatal respiratory distress, particularly if the patient is unconscious or is not being closely monitored by medical personnel.

Figure 2:
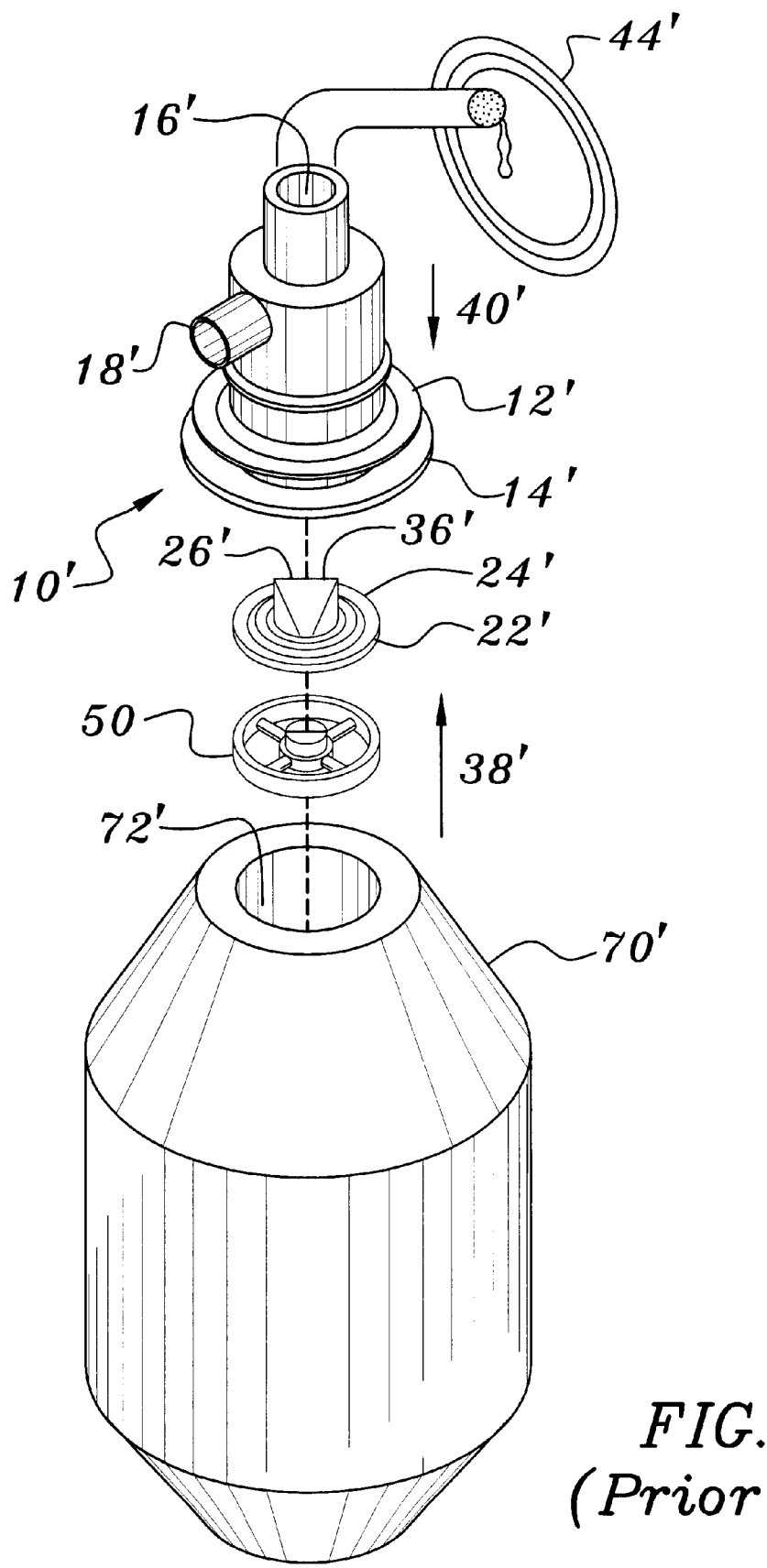
FIG. 2 is an exploded view of a conventional duck-bill NRV attached to a breathing assistance apparatus with a retainer ring.

To avoid potential inversion of the inner portion 26, it has been suggested to provide means upstream of the duck-bill valve 22 to support the duck-bill valve 22 when it is subjected to extreme back pressures that may be exerted by the patient. An example of such an arrangement is shown in FIG. 2. The NRV of that figure is identified by reference numeral 10' and is constructed and functions substantially similarly to the NRV 10 discussed hereinabove. Hence, the components of NRV 10' which have the same reference numerals as components identified in FIGS. 1 and 1A, but which are distinguished by prime symbols, may be considered to be the substantial equivalents in structure and function to their counterparts in FIGS. 1 and 1A and thus will not be described in detail. For brevity, therefore, only that structure in FIG. 2 which materially departs in structure and/or function from that disclosed in FIGS. 1 and 1A will be addressed here below.

In this regard, the primary distinction between NRV 10 and NRV 10' is the provision of a retainer ring 50 which is positioned adjacent to duck-bill valve 22. The retainer ring 50 has been previously disclosed in the prior art. It typically assumes the form of a cage-like retainer ring or a grate which resists inversion of the inner portion 26, but which includes one or more openings to permit the passage of respiratory gas 38.

It is important to note that the retainer ring 50 of the prior art only functions to prevent the duck-bill valve 22 from inverting. In the prior art, retainer ring 50 is made of a hard plastic material and is designed not to flex in response to the duck-bill valve 22.

Figure 3:
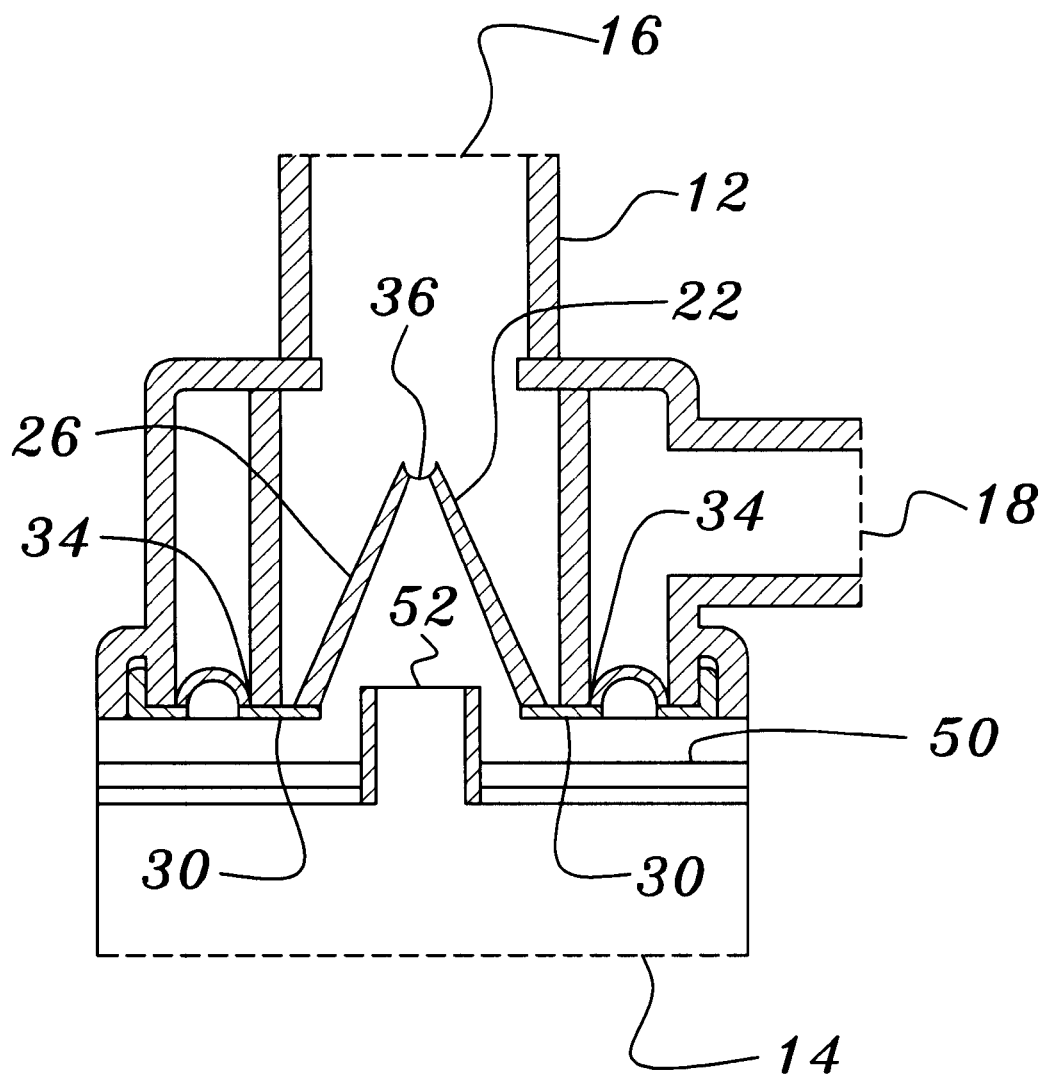
FIG. 3 is a cross-sectional view of the prior art wherein the duck-bill portion of the NRV valve element is shown in a non-use position in conjunction with a conventional retainer ring.

As is best shown in FIG. 3, the retainer ring 50 of the prior art is positioned between the first opening of the valve housing 12 and the duck-bill valve 22. In FIG. 3, the duck-bill valve 22 is in the seated position, meaning that the sealing portion 30 is in sealing contact with the internal valve housing seat 34. When the duck-bill valve 22 is in the seated position, a first fluid or respiratory gas that flows into the first opening 14 can only flow out of the second opening 16. As is shown in FIG. 3, the center portion 52 of the retainer ring 50 of the prior art is in close proximity to the inner portion 26 of the duck-bill valve 22. This feature of the retainer ring 50 is important because the duck-bill valve 22 could invert if the retainer ring 50 was not present when a second fluid or expiratory gas flowed into the second opening 16 and impinged on the duck-bill valve 22. When the second fluid or expiratory gas strikes the duck-bill valve 22, the sealing portion 30 unseats from the internal valve housing seat 34. This unseated position allows the second fluid or expiratory gas to flow only out of the exhaust port 18. However, it is important to note, that the retainer ring 50 of the prior art only allows the sealing portion 30 to unseat from the internal valve housing seat 34 a small distance. This small distance only allows a small amount of the second fluid or expiratory gas to be exhausted through exhaust port 18.

Figures 4A, 4B:
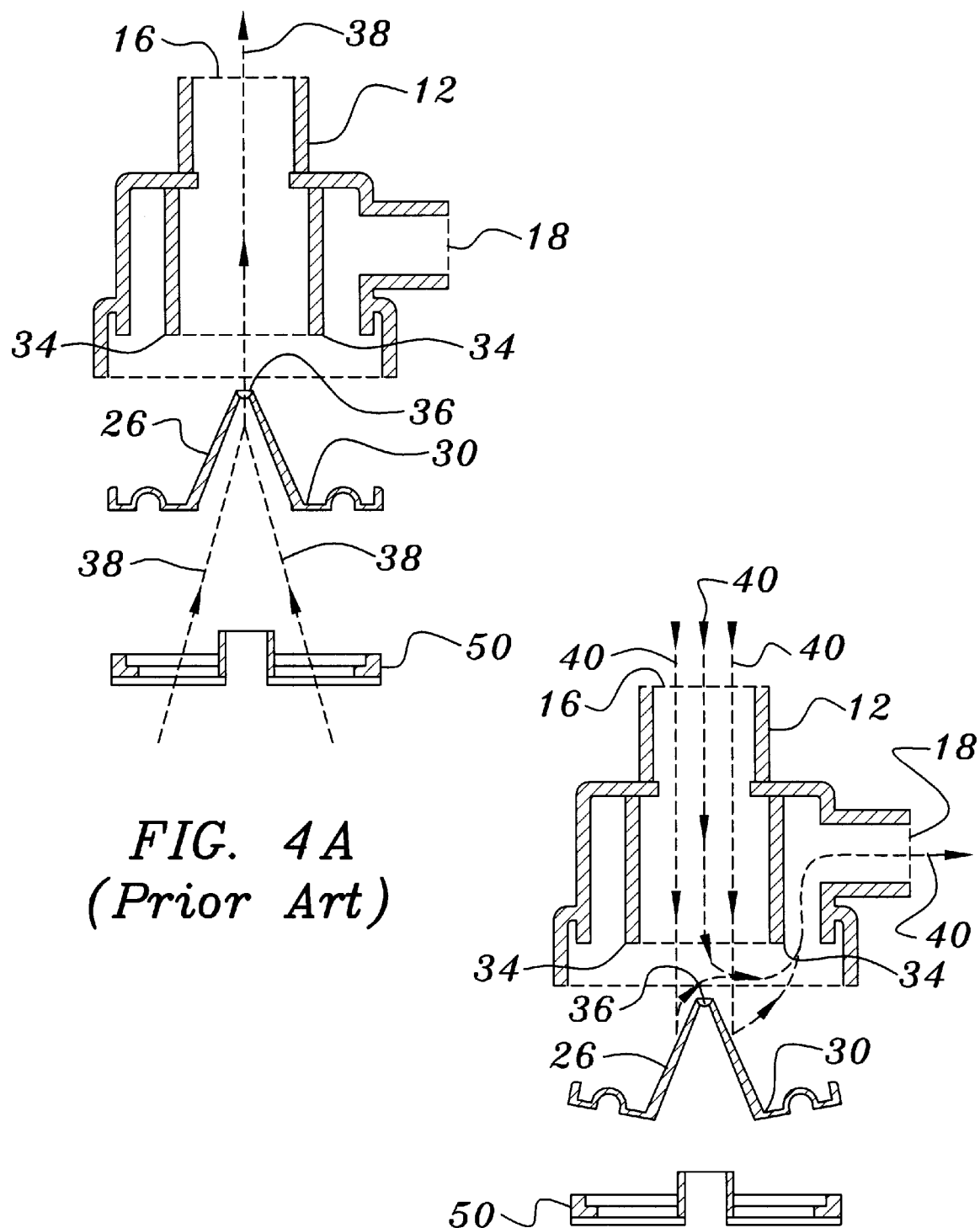
FIG. 4A is an exploded cross-sectional view of the prior art wherein the duck-bill portion of the NRV valve element is shown in normal operation during the flow of a respiratory gas in conjunction with a conventional retainer ring.
FIG. 4B is an exploded cross-sectional view of the prior art wherein the duck-bill portion of the NRV valve element is shown in normal operation during the flow of an expiratory gas in conjunction with a conventional retainer ring.

FIG. 4A is an exploded cross-sectional view of the valve housing 12 showing the retainer ring 50 of the prior art and the duck-bill valve 22 in positions adjacent to their actual respective positions. In FIG. 4A, the first fluid or respiratory gas 38 is flowing through the retainer ring 50 and impinges upon the inside surface of the inner portion 26 of the duck-bill valve 22. The first fluid or respiratory gas 38 forces open the small slot 36 of the duck-bill valve 22 and forces the sealing portion 30 to remain in sealing contact with the internal valve housing seat 34. Accordingly, the first fluid or respiratory gas 38 is then forced to travel through the duck-bill valve 22 and only out of the second opening 16 of the valve housing 12. Note, the retainer ring 50 of the prior art serves no purpose when only the first fluid or respiratory gas 38 is flowing.

FIG. 4B is an exploded cross-sectional view of the valve housing 12 showing the retainer ring 50 of the prior art and the duck-bill valve 22 in positions adjacent to their actual respective positions. In FIG. 4B, the second fluid or expiratory gas 40 is flowing through the second opening 16 and impinges upon the outside surface of the inner portion 26 of the duck-bill valve 22. The second fluid or expiratory gas 40 forces closed the small slot 36 of the duck-bill valve 22 and forces the sealing portion 30 to unseat a small distance from the internal valve housing seat 34. Accordingly, the second fluid or expiratory gas 40 is then forced to travel through the small space created by the unseating of the sealing portion 30 from the internal valve housing 34 and only out of the exhaust port 18 of the valve housing 12. Note, the retainer ring 50 of the prior art only functions to prevent inversion of the duck-bill valve in response to a forceful flow of the second fluid or expiratory gas 40.

Figure 5A:
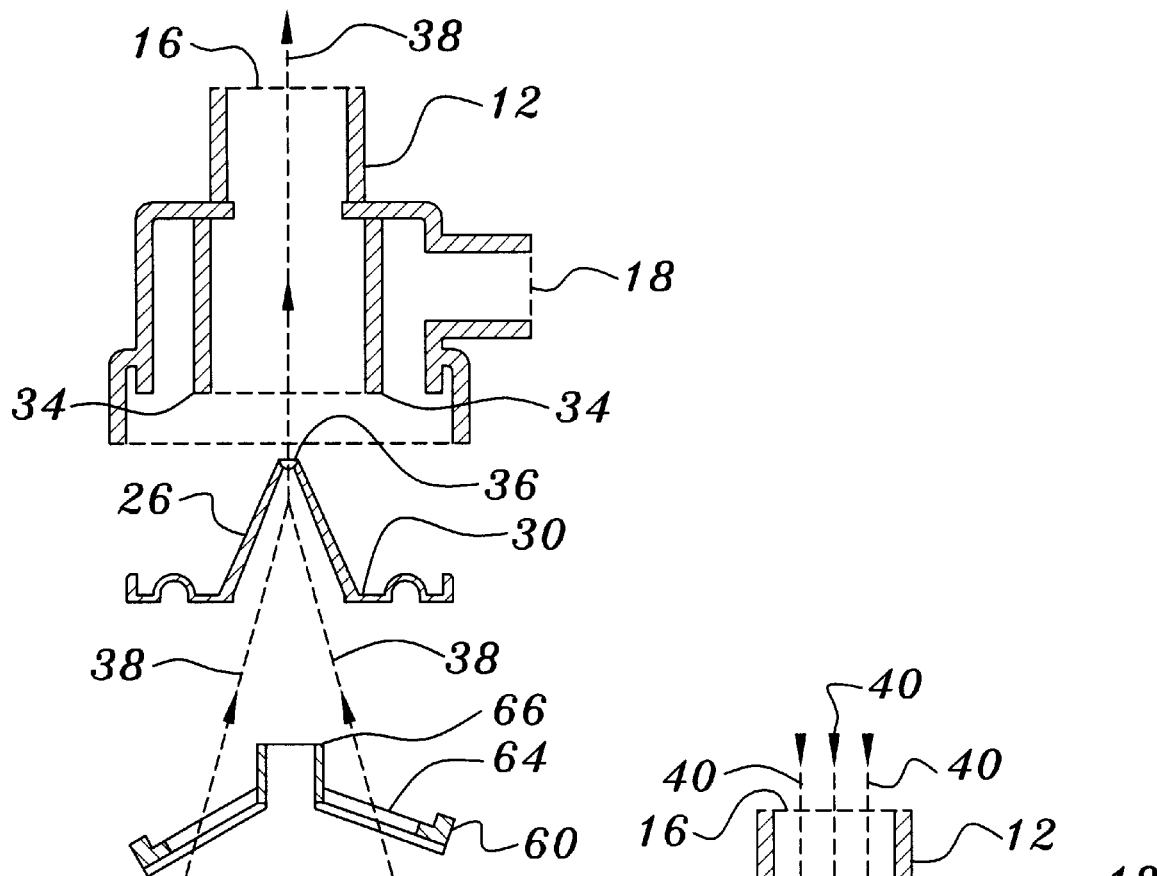
FIG. 5A is an exploded cross-sectional view of the present invention wherein the duck-bill portion of the NRV valve element is shown in normal operation during the flow of a respiratory gas in conjunction with a retainer ring of the present invention.

FIG. 5A is an exploded cross-sectional view of the valve housing 12 showing the flexible retainer ring 60 of the present invention and the duck-bill valve 22 in positions adjacent to their actual respective positions. In FIG. 5A, the first fluid or respiratory gas 38 is flowing through the flexible retainer ring 60 and impinges upon the inside surface of the inner portion 26 of the duck-bill valve 22. The first fluid or respiratory gas 38 forces open the small slot 36 of the duck-bill valve 22 and forces the sealing portion 30 to remain in sealing contact with the internal valve housing seat 34. Accordingly, the first fluid or respiratory gas 38 is then forced to travel through the duck-bill valve 22 and only out of the second opening 16 of the valve housing 12. Note, the flexible retainer ring 60 of the present invention assists in the opening of the small slot 36 of the duck-bill valve 22 by pushing against the inside surface of inner portion 26 in response to the flow of first fluid or respiratory gas 38. The flexible retainer ring 60 of the present invention is able to assist in the opening of the small slot 36 of the duck-bill valve 22 because of the flexible supports 64 that are connected to the center portion 66, allowing the center portion 66 to deflect towards the small slot 36 in response to the flow of the first fluid or respiratory gas 38. Further, the center portion 66 of the flexible retainer ring 60 is of a substantial width and depth to seat within the inner portion 26 of the duck-bill valve 22.

Figure 5B:
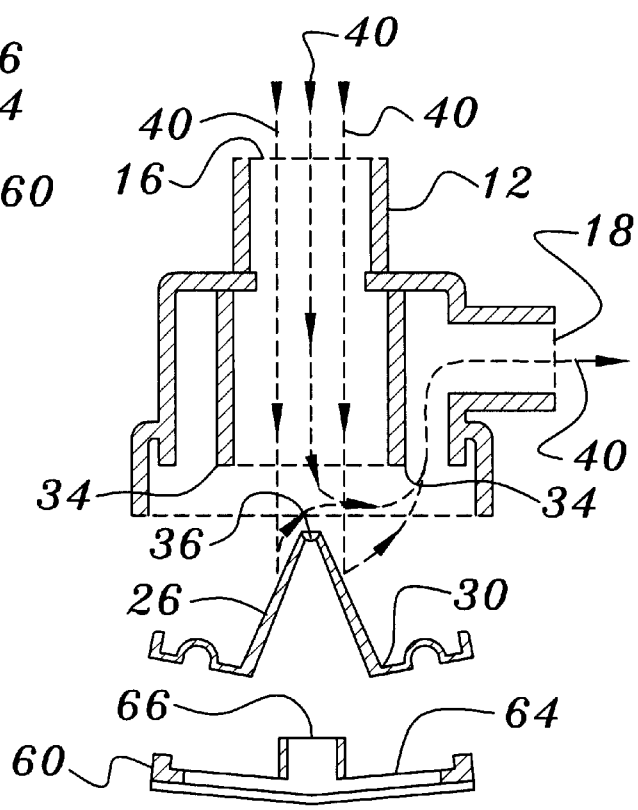
FIG. 5B is an exploded cross-sectional view of the present invention wherein the duck-bill portion of the NRV valve element is shown in normal operation during the flow of an expiratory gas in conjunction with a retainer ring of the present invention.

FIG. 5B is an exploded cross-sectional view of the valve housing 12 showing the flexible retainer ring 60 of the present invention and the duck-bill valve 22 in positions adjacent to their actual respective positions. In FIG. 5B the second fluid or expiratory gas 40 is flowing through the second opening 16 and impinges upon the outside surface of the inner portion 26 of the duck-bill valve 22. The second fluid or expiratory gas 40 forces closed the small slot 36 of the duck-bill valve 22 and forces the sealing portion 30 to unseat from the internal valve housing seat 34. Accordingly, the second fluid or expiratory gas 40 is then forced to travel through the space created by the unseating of the sealing portion 30 from the internal valve housing seat 34 and only out of the exhaust port 18 of the valve housing 12. Note, the flexible retainer ring 60 of the present invention also prevents inversion of the duck-bill valve 22 in response to a forceful flow of the second fluid or expiratory gas 40. In addition, the flexible retainer ring 60 of the present invention is able to prevent distortion and act as a shock absorber for the inner portion 26 of the duck-bill valve 22 because of the flexible supports 64 that are connected to the center portion 66 allowing the center portion 66 to deflect with the inner portion 26 in response to the flow of the first fluid or respiratory gas 38.

Most importantly, the flexible retainer ring 60 of the present invention allows the sealing portion 30 to unseat a greater distance from the internal valve housing seat 34. Accordingly, a greater amount of the second fluid or expiratory gas 40 can travel through the larger space created by the unseating of the sealing portion 30 from the internal valve housing 34 and only out of the exhaust port 18 of the valve housing 12. The flexible retainer ring 60 of the present invention is able to allow the sealing portion 30 to unseat a greater distance from the internal valve housing 34 while still preventing inversion of the duck-bill valve 22. The flexible retainer ring 60 of the present invention is able to allow the sealing portion 30 to unseat a greater distance from the internal valve housing 34 because of the flexible supports 64 that are connected to the center portion 66, allowing the center portion 66 to deflect with the inner portion 26 of the duck-bill valve 22 in response to the flow of the second fluid or expiratory gas 40.

Figure 6A:
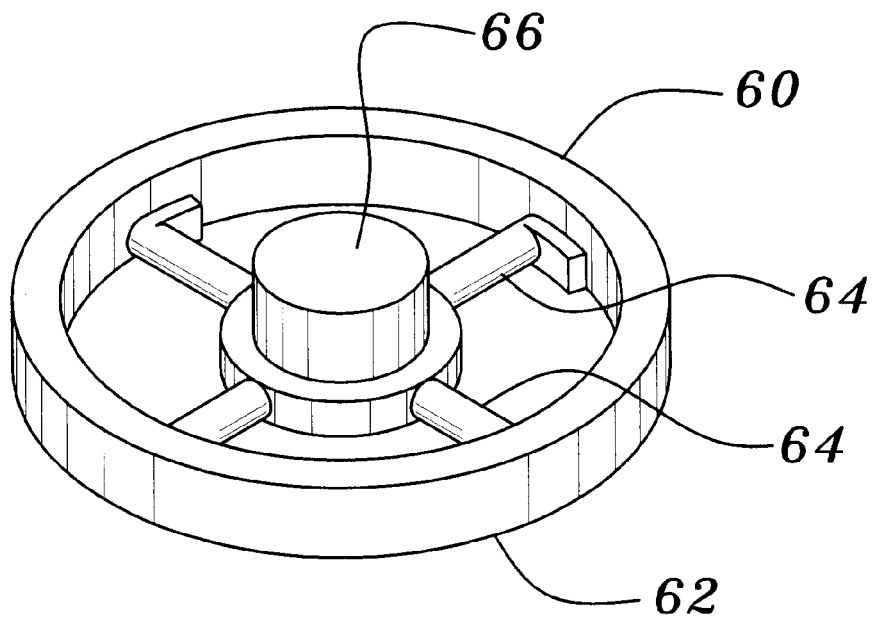
FIG. 6A is a blown up view of the flexible retainer ring showing the flexible supports.
Figure 6B:
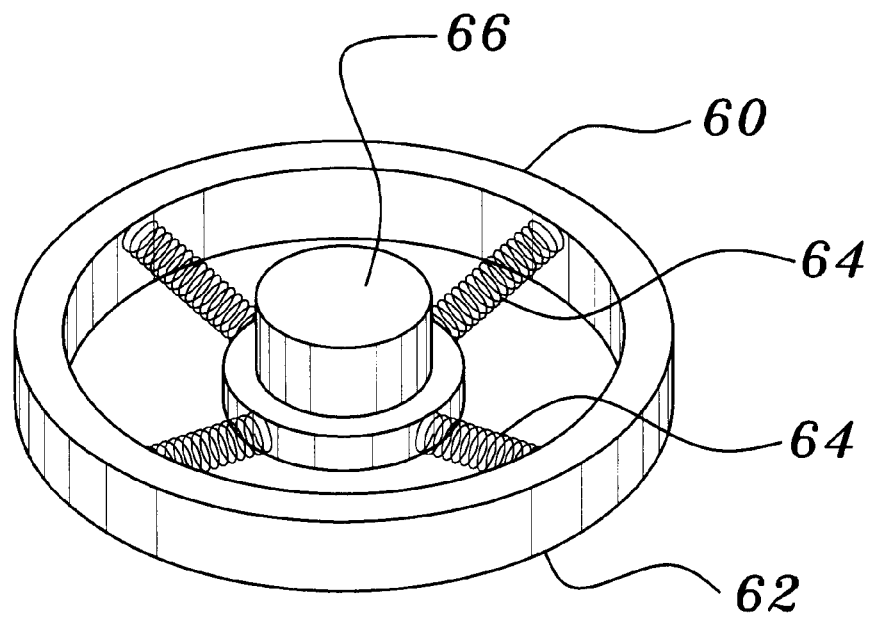
FIG. 6B is a blown up view of the flexible retainer ring showing the flexible supports being made from springs.

As is best shown in FIG. 6A, the flexible retainer ring 60 of the present invention comprises a thin substantially circular portion 62 for attaching to the valve housing 12; a plurality of flexible supports 64 extending radially inward from the circular portion 62; and a center portion 66. In one embodiment, the plurality of flexible supports 64 can be made from silicone rubber. In an alternative embodiment, as best shown in FIG. 6B, the plurality of flexible supports 64 of the flexible ring 60 can be made of springs.

The flexible retainer ring of the present invention thus provides a novel NRV or one-way valve. The flexible retainer ring of the present invention allows the valve housing to be made smaller than a conventional valve housing while maintaining the necessary flow rate for expiratory gas through the exhaust port of the valve housing. This smaller housing can be extremely useful in the care of infants and neonatal patients or in industrial applications requiring smaller instruments. Further, the flexible retainer ring offers increased protection against inversion and effectively maintains the integrity of the one-way valve element while producing an assembly of uncomplicated yet rugged design, comparatively low cost to manufacture and reliable operation.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. An improved non-rebreathing valve for use in breathing apparatus, comprising in combination:

a valve housing having a first opening at one end, a second opening at an opposite end, an exhaust port in between said first opening and said second opening, and an internal valve housing seat;

a one-way valve element disposed in said valve housing between said first opening and said exhaust port, said one-way valve element in sealing contact with said internal valve housing seat of said valve housing to allow a respiratory gas flowing into said first opening of said valve housing to flow through said one-way valve element and only out of said second opening of said valve housing and to allow an expiratory gas to unseat said one-way valve element from said internal valve housing seat of said valve housing to allow the expiratory gas to flow into said exhaust port of said valve housing; and a retainer ring positioned in said valve housing between said one-way valve element and said first opening, said retainer ring having a center portion and an annular ring portion, said center portion being concentrically connected within said annular ring portion by a plurality of flexible radial supports extending in a radial direction from said center portion to said annular ring portion allowing said center portion to flex axially relative to said annular ring portion (1) during the flow of said expiratory gas and resiliently assists in the displacement of said one-way valve element from said internal valve housing seat thereby increasing, toward said first opening to a first extended position upon being engaged by said one-way valve element and to provide resilient shock absorption for said one-way valve element as said one-way valve element moves axially toward said first opening after being unseated from said internal valve housing seat to thereby increase the flow of said expiratory gas to said exhaust port of said valve housing while preventing inversion and deformation of said one-way valve element in response to the flow of said expiratory gas, and (2) during the flow of said respiratory gas, toward said second opening to a second extended position to engage said one-way valve element to assist in the opening of said one-way valve element as said one-way valve element moves axially toward said second opening to thereby increase the flow of said respiratory through said one-way valve element.

2. The non-rebreathing valve according to claim 1, wherein said one-way valve element further comprises:

an outer peripheral portion continuously and sealingly affixed to said valve housing;

an inner portion that projects in the direction of the flow of said respiratory gas;

a sealing portion extending radially inward from and contiguous with said peripheral portion, said sealing portion contacting said internal valve housing seat of said valve housing; and a small slot at a distal end to said inner portion, said slot allowing said respiratory gas to flow through said one-way valve.

3. The non-rebreathing valve according to claim 2, wherein said inner portion of said one-way valve element further comprises a hollow, wedge-shaped formation that generally resembles the shape of a duck-bill.

4. The non-rebreathing valve according to claim 3, wherein said one-way valve element further having a generally semi-toroidal region for rendering the one-way valve element less resistant to the pressure generated by said expiratory gas.

5. The non-rebreathing valve according to claim 4, wherein said center portion of said flexible retainer ring further having a substantial width and depth to seat within said inner portion of said one-way valve element and said center portion of said flexible retainer ring resiliently assists in opening said small slot of said one-way valve element in response to the flow of said respiratory gas thereby increasing the flow of said respiratory gas.

6. The non-rebreathing valve according to claim 5, wherein said flexible retainer ring being formed from silicone rubber.

7. The non-rebreathing valve according to claim 5, wherein said plurality of flexible supports of said flexible retainer ring being a plurality of springs.

8. An improved one-way valve, comprising in combination:

a valve housing having a first opening at one end, a second opening at an opposite end, an exhaust port in between said first opening and said second opening, and an internal valve housing seat;

a one-way valve element disposed in said valve housing between said first opening and said exhaust port, said one-way valve element in sealing contact with said internal valve housing seat of said valve housing to allow a first fluid flowing into said first opening of said valve housing to flow through said one-way valve element and only out of said second opening of said valve housing and to allow a second fluid to unseat said one-way valve element from said internal valve housing seat of said valve housing to allow the second fluid to flow into said exhaust port of said valve housing; and a retainer ring positioned in said valve housing between said one-way valve element and said first opening, said retainer ring having a center portion and an annular ring portion, said center portion being concentrically connected within said annular ring portion by a plurality of flexible radial supports extending in a radial direction from said center portion to said annular ring portion allowing said center portion to flex axially relative to said annular ring portion said flexible retainer ring provides shock absorption for said one-way valve element (1) during the flow of said second fluid and resiliently assists in the displacement of said one-way valve element from said internal valve housing seat thereby increasing, toward said first opening to a first extended position upon being engaged by said one-way valve element and to provide resilient shock absorption for said one-way valve element as said one-way valve element moves axially toward said first opening after being unseated from said internal valve housing seat to thereby increase the flow of said second fluid to said exhaust port of said valve housing while preventing inversion and deformation of said one-way valve element in response to the flow of said second fluid, and (2) during the flow of said first fluid, toward said second opening to a second extended position to engage said one-way valve element to assist in the opening of said one-way valve element as said one-way valve element moves axially toward said second opening to thereby increase the flow of said first fluid through said one-way valve element.

9. The one-way valve according to claim 8, wherein said one-way valve element further comprises:

an outer peripheral portion continuously and sealingly affixed to said valve housing;

an inner portion that projects in the direction of the flow of said first fluid;

a sealing portion extending radially inward from and contiguous with said peripheral portion, said sealing portion contacting said internal valve housing seat of said valve housing; and a small slot at a distal end to said inner portion, said slot allowing said first fluid to flow through said one-way valve.

10. The one-way valve according to claim 9, wherein said inner portion of said one-way valve element further comprises a hollow, wedge-shaped formation that generally resembles the shape of a duck-bill.

11. The one-way valve according to claim 10, wherein said one-way valve element further having a generally semi-toroidal region for rendering the one-way valve element less resistant to the pressure generated by said second fluid.

12. The one-way valve according to claim 10, wherein said center portion of said flexible retainer ring further having a substantial width and depth to seat within said inner portion of said one-way valve element and said center portion of said flexible retainer ring resiliently assists in opening said small slot of said one-way valve element in response to the flow of said first fluid thereby increasing the flow of said first fluid.

13. The one-way valve according to claim 12, wherein said flexible retainer ring being formed from silicone rubber.

14. The one-way valve according to claim 12, wherein said plurality of flexible supports of said flexible retainer ring being a plurality of springs.

* * * * *

UNITED STATES PATENT AND TRADEMARK OFFICE
CERTIFICATE OF CORRECTION

PATENT NO. : 6,527,011 B1
DATED : March 4, 2003
INVENTOR(S) : Mantz, Robert F.

It is certified that error appears in the above-identified patent and that said Letters Patent is hereby corrected as shown below:

Column 9,
Line 33, please delete "and resiliently assists in the displacement of said one-way valve element from said internal valve housing seat thereby increasing"

Column 10,
Lines 11 and 14, delete the word "flexible"
Lines 19 and 22, delete the word "flexible"
Line 24, delete the word "one-way"
Line 51, delete "said flexible retainer ring provides shock absorption for said one-way valve element"
Line 53, delete "and resiliently assists in the displacement of said one-way valve element from said internal valve housing seat thereby increasing"

Column 11,
Lines 6 and 20, delete "one-way"

Column 12,
Lines 1, 7, 16 and 19, delete "one-way"
Lines 8, 11, 17 and 20, delete "flexible"

Signed and Sealed this

Twelfth Day of August, 2003

JAMES E. ROGAN
*Director of the United States Patent and Trademark Office*